United States Patent [19]

Suzuki

[11] Patent Number: 5,335,665
[45] Date of Patent: Aug. 9, 1994

[54] METHOD OF MEASURING BLOOD PRESSURE, AND AUTOMATIC SPHYGMOMANOMETER FOR IMPLEMENTING SAID METHOD

[75] Inventor: Seigo Suzuki, Fuji, Japan

[73] Assignee: Terumo Kabushiki Kaisha, Tokyo, Japan

[21] Appl. No.: 845,067

[22] Filed: Mar. 3, 1992

[30] Foreign Application Priority Data

Mar. 7, 1991 [JP] Japan .................. 3-041522

[51] Int. Cl.⁵ .............................. A61B 5/02
[52] U.S. Cl. ........................... 128/680; 128/681; 364/413.03
[58] Field of Search ............... 128/677–686; 364/412.03

[56] References Cited

U.S. PATENT DOCUMENTS

| | | | |
|---|---|---|---|
| 4,009,709 | 3/1977 | Link et al. | |
| 4,754,761 | 7/1988 | Ramsey, III et al. | 128/681 |
| 4,830,019 | 5/1989 | Shirasaki et al. | |
| 5,094,245 | 3/1992 | Shirasky | 128/680 |
| 5,103,830 | 4/1992 | Shinomiya | 128/681 |

FOREIGN PATENT DOCUMENTS

| | | |
|---|---|---|
| 59-19692 | 5/1984 | Japan . |
| 60-40038 | 3/1985 | Japan . |
| 61-4-416 | 9/1986 | Japan . |
| 62-292139 | 12/1987 | Japan . |

OTHER PUBLICATIONS

The Journal of Clinical Engineering–Jul./Aug. 1987, vol. 12, No. 4, pp. 297–303, Indirect Measurement of Arterial Pressure in the Limbs of Babies & Children by the volume Oscillometric Method.

Primary Examiner—Kyle L. Howell
Assistant Examiner—Robert L. Nasser
Attorney, Agent, or Firm—Frishauf, Holtz, Goodman & Woodward

[57] ABSTRACT

A method of measuring blood pressure, and an automatic sphygmomanometer for implementing this method, whereby an appropriate value of cuff inflation is achieved which is dependent upon the systolic blood pressure of a patient. Pulse waves are extracted from cuff pressure obtained through a pressure detector during inflation of the cuff, and the rate of change in the amplitude of the pulse waves is obtained by a control unit. When the rate of change obtained has exceeded a predetermined threshold value, it is judged that the internal cuff pressure has surpassed the patient's systolic blood pressure. In response, inflation of the cuff by means of a pump is terminated.

7 Claims, 8 Drawing Sheets

METHOD OF MEASURING BLOOD PRESSURE, AND AUTOMATIC SPHYGMOMANOMETER FOR IMPLEMENTING SAID METHOD

BACKGROUND OF THE INVENTION

1. Field of the Invention

This invention relates to a method of measuring blood pressure and an automatic sphygmomanometer for implementing this method. More particularly, the invention relates to a method of measuring blood pressure and an automatic sphygmomanometer in which an appropriate value of pressurization is capable of being detected automatically.

2. Prior Art

A well-known method of measuring blood pressure includes the oscillometric method in which oscillation (referred to as a "pulse wave") produced when blood flows through a blood vessel is detected and the value of blood pressure is determined by a change in the state of the pulse wave. In accordance with this method, it is necessary to know the amplitude of the pulse wave, the change thereof and the characteristics of the waveform. Therefore, when blood pressure is measured, first the internal pressure of a cuff wound upon the patient's arm is elevated to a value 30 to 40 mmHg higher than that of the patient's systolic blood pressure or maximum blood pressure, then the cuff pressure is gradually reduced to obtain a waveform, of the kind shown in FIG. 7, indicating the change in the pulse wave with the passage of time. As shown in FIG. 7, the amplitude of the pulse wave gradually increases with respect to time, but then its amplitude decreases after it reaches a certain point. It is known that cuff pressure at the time of maximum amplitude of the pulse wave is the mean blood pressure.

Thus, when blood pressure is measured in this manner, the interior of the cuff is required to be pressurized so that its internal pressure exceeds the patient's systolic blood pressure by 30 to 40 mmHg. For this reason, the conventional sphygmomanometer is provided with a switch so that different values of increased pressure (e.g., 140, 170, 200, 240 mmHg) can be set, and the patient makes use of the switch to select and set a suitable value of increased pressure depending upon the patient's own systolic blood pressure value.

However, the prior art described above has certain disadvantages. For example, if the patient does not have a rough idea of his or her own blood pressure, or if the value of pressurization selected is inappropriate, the pressure of the cuff may be inadequate or, conversely, the pressure of the cuff may be too high. In addition, the switch provided on the sphygmomanometer for setting different values of pressurization is capable of setting these values in stages only. For example, if the values can only be set in the manner described earlier, then a patient whose systolic blood pressure is 120 mmHg must pressurize the pressure of the cuff to 170 mmHg. Pressurization to this extent can cause the patient discomfort.

In an effort to solve the foregoing problems, Japanese Patent Application Laid-Open No. 60-40038 discloses a technique in which the mean blood-pressure value is obtained during increase of the internal pressure of the cuff or inflation of the cuff and an appropriate value of pressurization is found based upon the mean value obtained. In this case, however, it is required that the rate at which the internal pressure of the cuff is raised be held at 5 mmHg/sec in consideration of the patient's pulse rate (60~70 beats/min), and in order to obtain the mean blood-pressure value in accurate fashion. As a consequence, an extended period of time is required to measure blood pressure. This places a considerable burden upon the patient. Furthermore, in order to obtain the mean blood-pressure value (absolute value), a calibration circuit is necessary. This inevitably results in a more complicated apparatus.

SUMMARY OF THE INVENTION

Accordingly, an object of the present invention is to provide an automatic sphygmomanometer capable of detecting an appropriate pressurization value automatically, and of measuring blood pressure in a short period of time.

According to the present invention, the foregoing object is attained by providing an automatic sphygmomanometer having a cuff affixed to a living body, pressurizing means for supplying the interior of the cuff with pressurized air, cuff-pressure detecting means for detecting the pressure of the pressurized air, and venting means for venting the pressurized air from the interior of the cuff, comprising pulse-wave detecting means for detecting pulse waves from the living body, based upon the cuff pressure detected by the cuff-pressure detecting means, during inflation (pressurization) of the cuff by the pressurizing means, and control means for picking up a change in the pulse waves and performing control, based upon the change in the pulse waves, in such a manner that inflation of the cuff by the pressurizing means is halted.

Another object of the present invention is to provide a method of measuring blood pressure, in which an appropriate pressurization value can be detected and the measurement can be performed in a short period of time.

According to the present invention, the foregoing object is attained by providing a method of measuring blood pressure comprising a pressurizing step of supplying the interior of a cuff, which has been affixed to a living body, with pressurized air in order to inflate the cuff, a detecting step of detecting pulse waves from the living body during inflation of the cuff, a calculating step of calculating a rate of change in the pulse waves based upon the pulse waves detected at the detecting step, a comparing step of comparing the rate of change in the pulse waves with a predetermined threshold value, a stopping step of stopping pressurization of the cuff based upon results of comparison performed by the comparing means, and a measuring step of measuring systolic blood pressure and/or diastolic blood pressure (minimum blood pressure) after pressurization of the cuff has been stopped.

In accordance with the present invention as described above, pulse waves are picked up from the living body during inflation of the cuff interior by the pressurizing means, and control is executed so that inflation of the cuff is halted based upon the change in the pulse waves.

The present invention is particularly advantageous since the cuff pressure is elevated at a high rate of pressurization, the pulse waves are detected during inflation of the cuff, and the appropriate value of inflation can be determined based upon the change in the waveform of the pulse waves. As a result, the optimum inflation of the cuff can be carried out at all times, and measurement of blood pressure can be performed in a short period of time. In addition, manual setting of blood-pressure values is no longer required.

Other features and advantages of the present invention will be apparent from the following description taken in conjunction with the accompanying drawings, in which like reference characters designate the same or similar parts throughout the Figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENT(S)

Preferred embodiments of the present invention will now be described in detail in accordance with the accompanying drawings.

[Description of the construction of the automatic sphygmomanometer]

Figure 1:
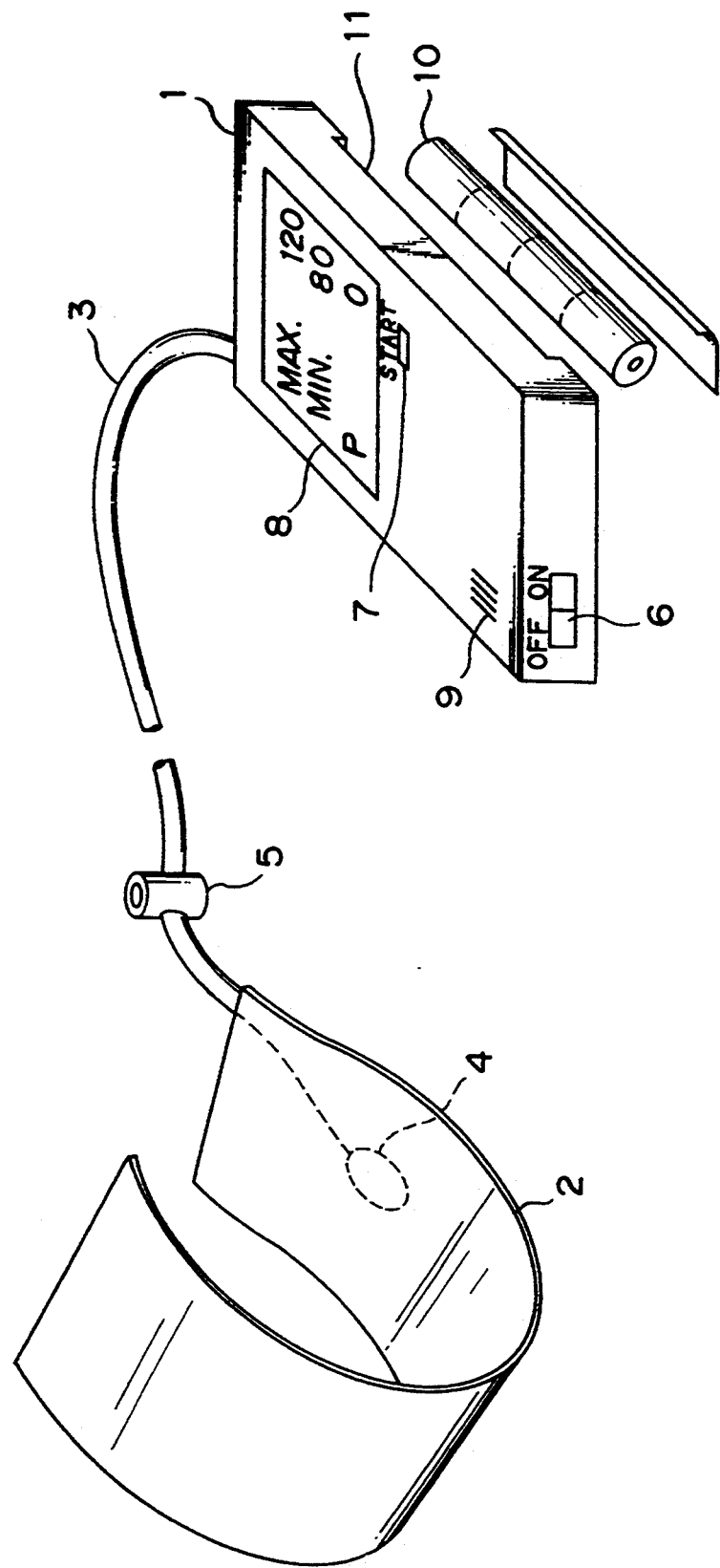
FIG. 1 is an external perspective view of an automatic sphygmomanometer illustrating a typical embodiment of the present invention.

FIG. 1 is an external perspective view of an automatic sphygmomanometer illustrating a typical embodiment of the present invention. As shown in FIG. 1, an automatic sphygmomanometer comprises a main body, a cuff 2 and a tube 3 interconnecting the main body and cuff. The cuff 2 has an internally provided microphone 4 for detecting Korotkoff sounds, and the tube 3 is provided with a constant-rate exhaust valve 5. The main body 1 is provided with a power-supply switch 6 for applying power to and cutting off power from the automatic sphygmomanometer, an indicator lamp 7 which indicates that measurement of blood pressure is in progress, an LCD (liquid-crystal display) 8 for displaying the results of measurement, and a buzzer 9. In this embodiment, the automatic sphygmomanometer employs dry cells 10 as the power supply. These are accommodated in a cell receptacle 11 of the main body 1.

The interior of the main body 1 is further provided with a inflating/deflating unit 20 for inflating and deflating the cuff 2, and a blood-pressure measurement control unit 30 for controlling the inflating and deflating of the cuff 2.

Figure 2A:
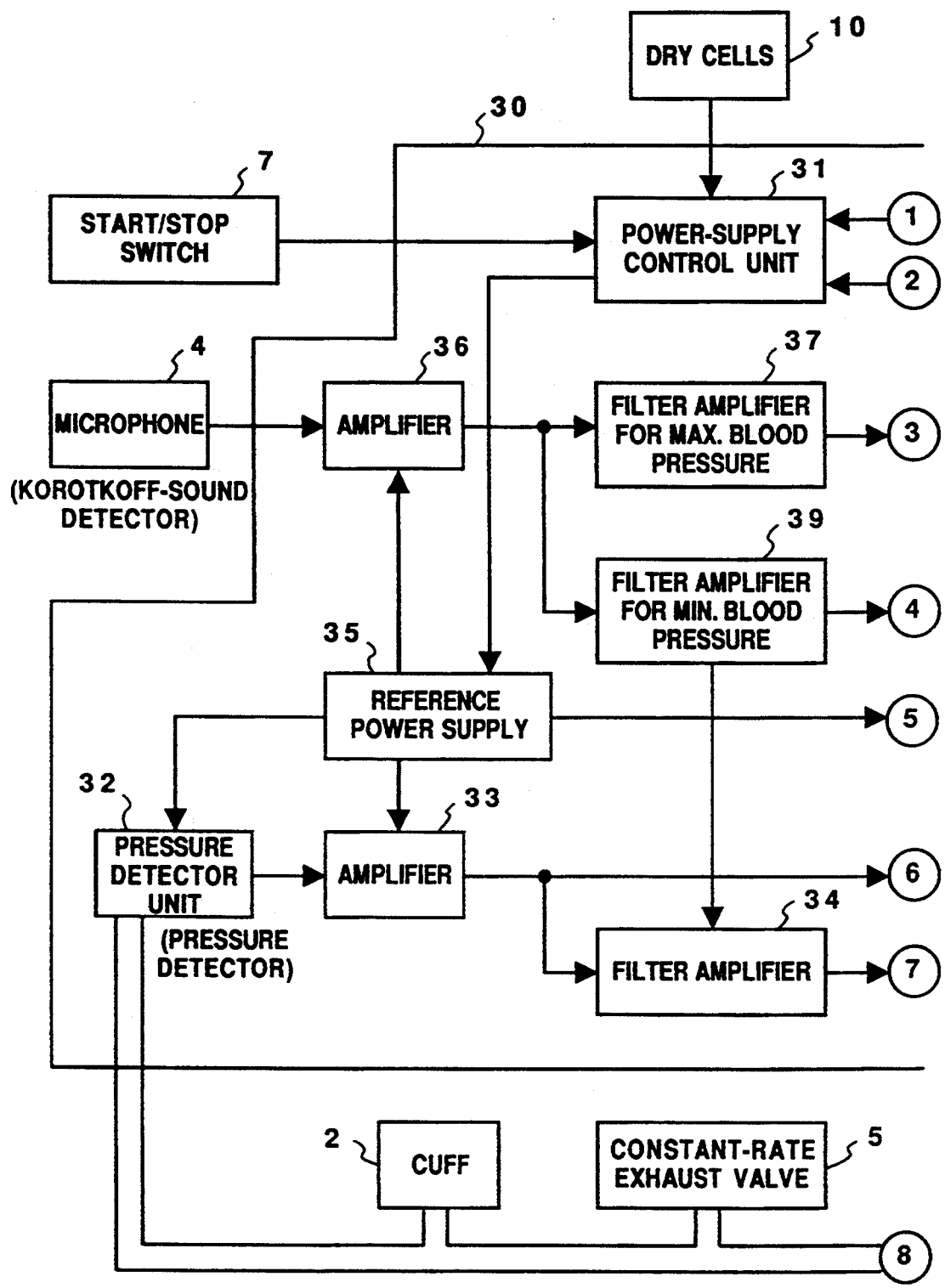
FIGS. 2A and 2B are block diagrams showing the construction of a inflating/deflating unit and blood-pressure measurement control unit constituting the main body of the automatic sphygmomanometer.
Figure 2B:
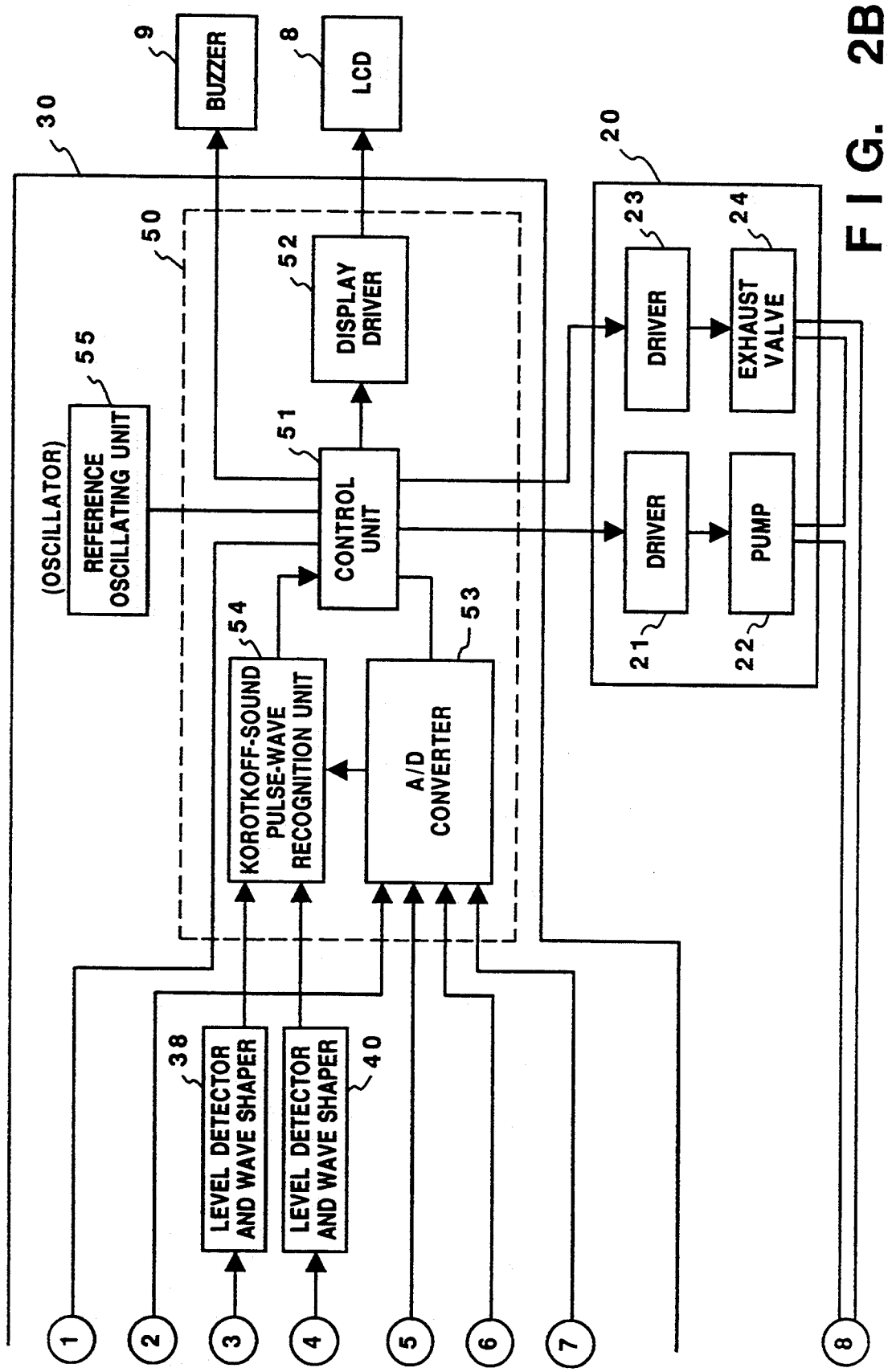

FIG. 2 is a block diagram illustrating the construction of the inflating/deflating unit 20 and the blood-pressure measurement control unit 30. As shown in FIG. 2, the inflating/deflating unit 20 comprises a driver 21 and a pump 22 for inflating the cuff 2, as well as a driver 23 and exhaust valve 24 for deflating the cuff 20. The blood-pressure measurement control unit 30 is equipped with power-supply controller 31 for controlling the supply of power to the entirety of the main body, a reference power-supply unit 35, a pressure detector 32 for detecting cuff pressure applied to a living body through the cuff 2, an operational amplifier 33 for amplifying an output from the pressure detector 32, a filter amplifier 34 for eliminating noise and extracting pulse waves from the output of the operational amplifier 33, and an operational amplifier 36 for amplifying Korotkoff sounds detected by the microphone 4.

The Korotkoff sounds detected by the microphone 4 are amplified by the operational amplifier 36, after which the amplified signal is fed into a filter amplifier 37 that is for recognizing systolic blood pressure, and a filter amplifier 39 that is for recognizing diastolic blood pressure (minimum blood pressure). The outputs of these amplifiers 37, 39 are wave-shaped by level detecting and wave shaping units 38, 40, respectively, and the outputs of the units 38, 40 are applied to a Korotkoff-sound pulse-wave recognition unit 54. Meanwhile, the cuff pressure detected by the pressure detector 32 and the pulse waves obtained through the filter amplifier 34 are fed into an A/D converter 53, where they are converted into digital signals. A controller 51 monitors the recognized Korotkoff sounds and the cuff pressure and controls the inflation and deflation of the cuff 2 through the drivers 21, 23 as necessary. Further, as necessary, the controller 51 causes the LCD 8 to display the value of systolic blood pressure, the value of diastolic blood pressure and the pulse rate through a display driver 52, and causes the buzzer 9 to emit sound.

Thus, with the automatic sphygmomanometer of this embodiment, cuff pressure and the change in the pulse waves are monitored in order to obtain the optimum value of pressurization, and the Korotkoff sounds are monitored in order to obtain the systolic and diastolic values of blood pressure. Accordingly, the method of measuring blood pressure according to this embodiment can be said to be a combination of the Korotkoff method and oscillometric method.

Method of Detecting Appropriate Value of Pressurization

Figure 3:
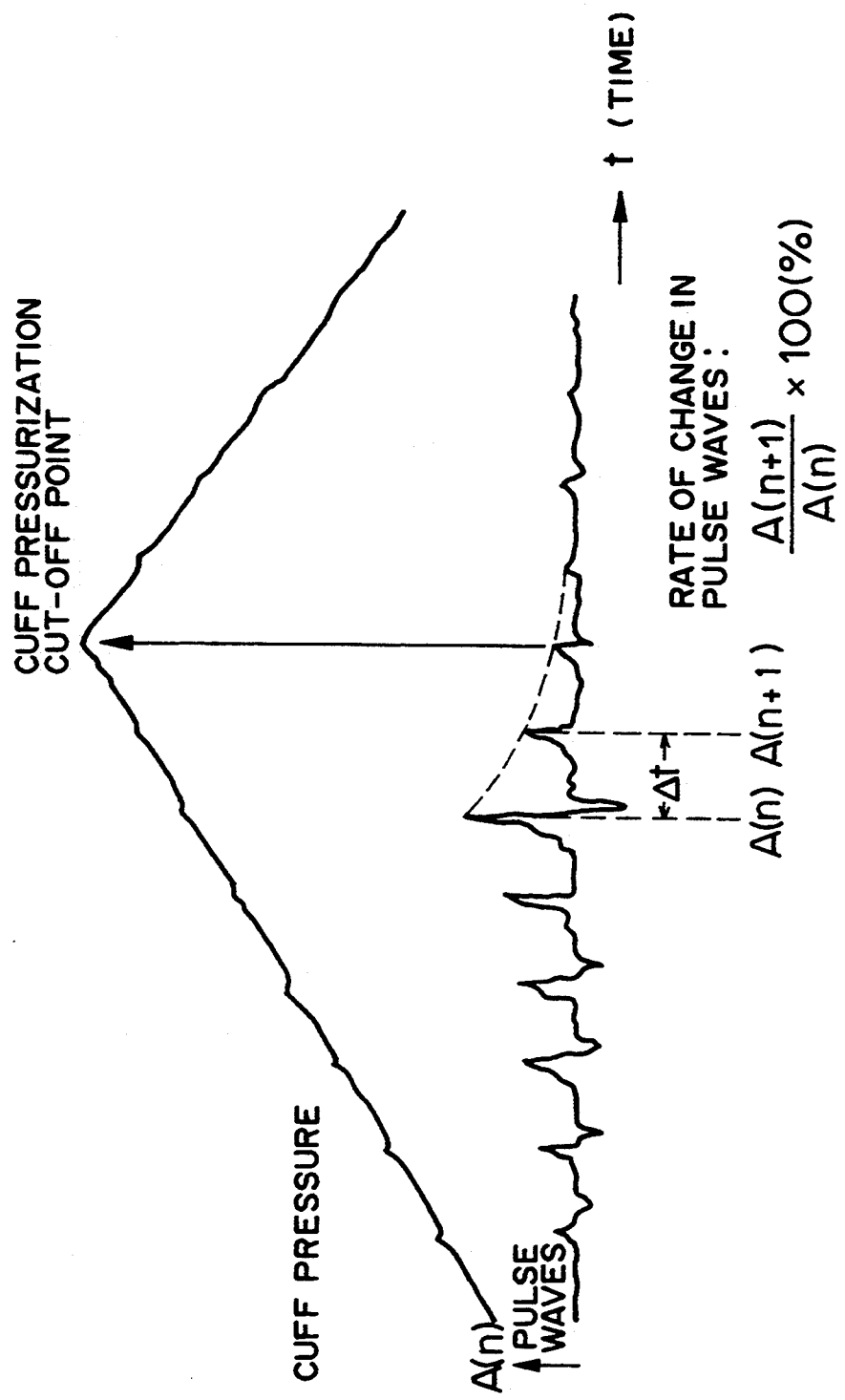
FIG. 3 is a diagram showing a change in pulse waves during a rise in cuff pressure.

In accordance with the prior art, pulse waves are detected during the decline in cuff pressure, and the systolic, diastolic and mean values of blood pressure are measured based upon the detected waveform. However, it is possible also to detect pulse waves during the increase in cuff pressure. FIG. 3 is a diagram illustrating the change in the pulse waves with time during the inflation of the cuff. During the process of the inflation of the cuff, the amplitude of the pulse waves gradually increases but then starts to decrease when a certain point is passed. It has been experimentally verified that the decrease in the amplitude of the pulse waves is particularly pronounced at the moment the point of systolic blood pressure is passed.

This fact is utilized in the present embodiment. Specifically, the pulse waves are detected during the rise in cuff pressure, a detected pulse wave is compared with the pulse wave of the immediately preceding beat and, when pulse-wave amplitude has diminished in excess of a predetermined level (found experimentally to be about 50~ about 70% of the pulse-wave amplitude which prevailed at the preceding beat), it is judged that the systolic blood pressure has been exceeded. Inflation of the cuff is then terminated. Thus, the appropriate value of pressurization can be found by detecting a sudden decline in the amplitude of the pulse waves. In addition, if measurement is performed in accordance with this method, it will suffice merely to take note of the change in amplitude from one pulse of the pulse waves to the next. Therefore, it is unnecessary to take suppression of the rate of inflation into consideration in order to obtain a mean value of blood pressure, and hence the cuff can be inflated at a high speed (30~40 mmHg/sec, by way of example). Furthermore, in terms of the circuit construction of the apparatus, the foregoing can be achieved by a mere differential circuit for obtaining the amount of change in amplitude, and it is possible to dispense with the calibration circuit required in the prior art for the purpose of obtaining the mean value of blood pressure.

Processing for Measuring Blood Pressure

Figure 4:
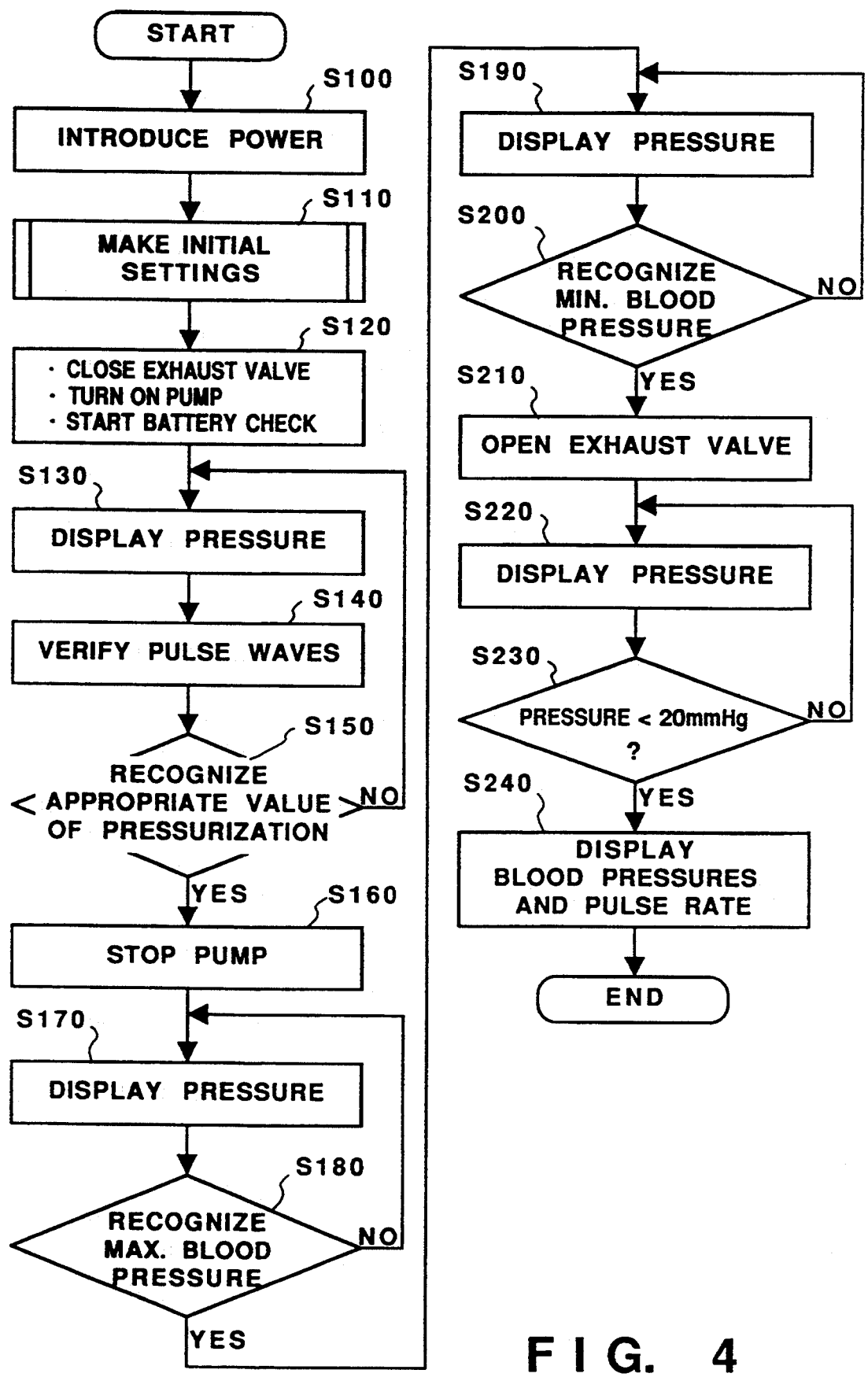
FIG. 4 is a flowchart showing processing for measuring blood pressure.
Figure 5:
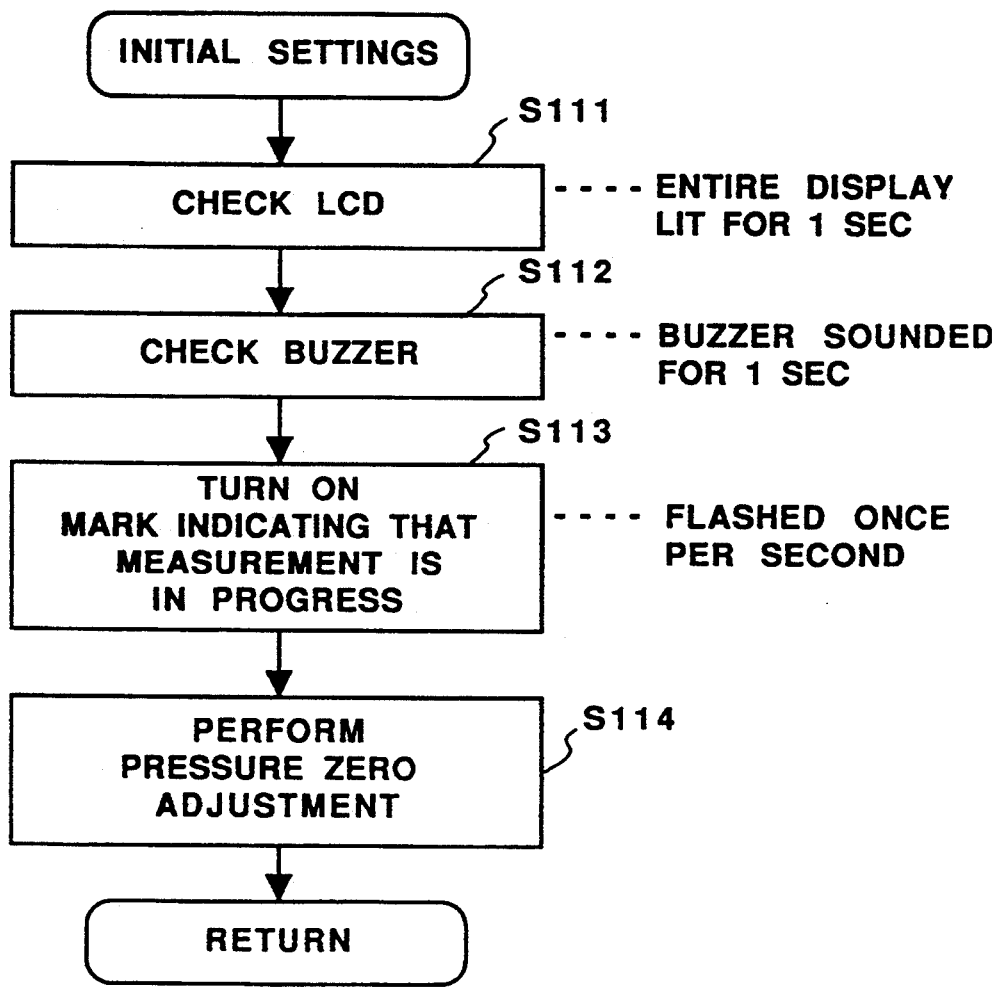
FIG. 5 is a flowchart showing processing for initially setting the automatic sphygmomanometer when blood pressure is measured.
Figure 6:
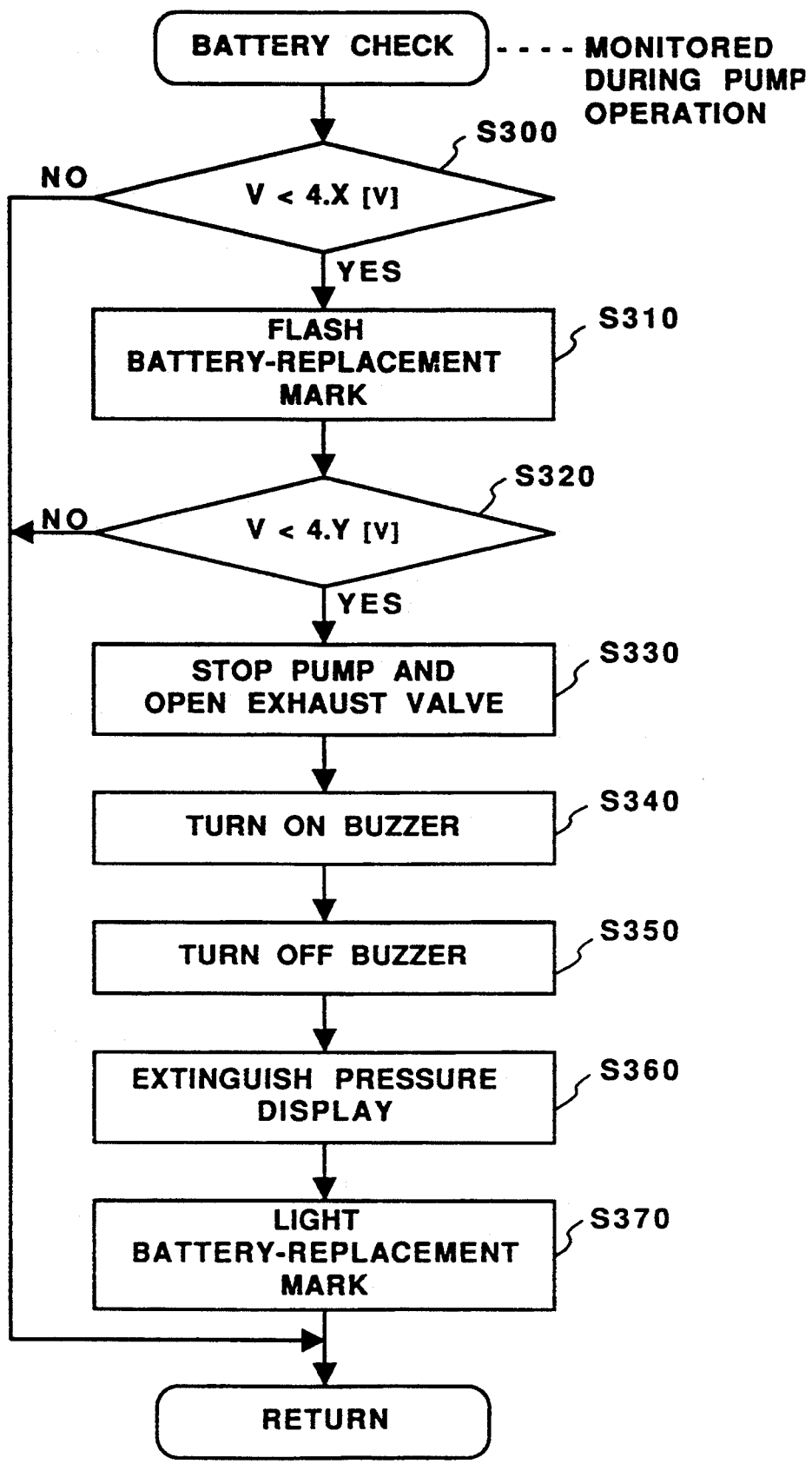
FIG. 6 is a flowchart showing battery-check monitoring processing performed by the automatic sphygmomanometer when blood pressure is measured.
Figure 7:
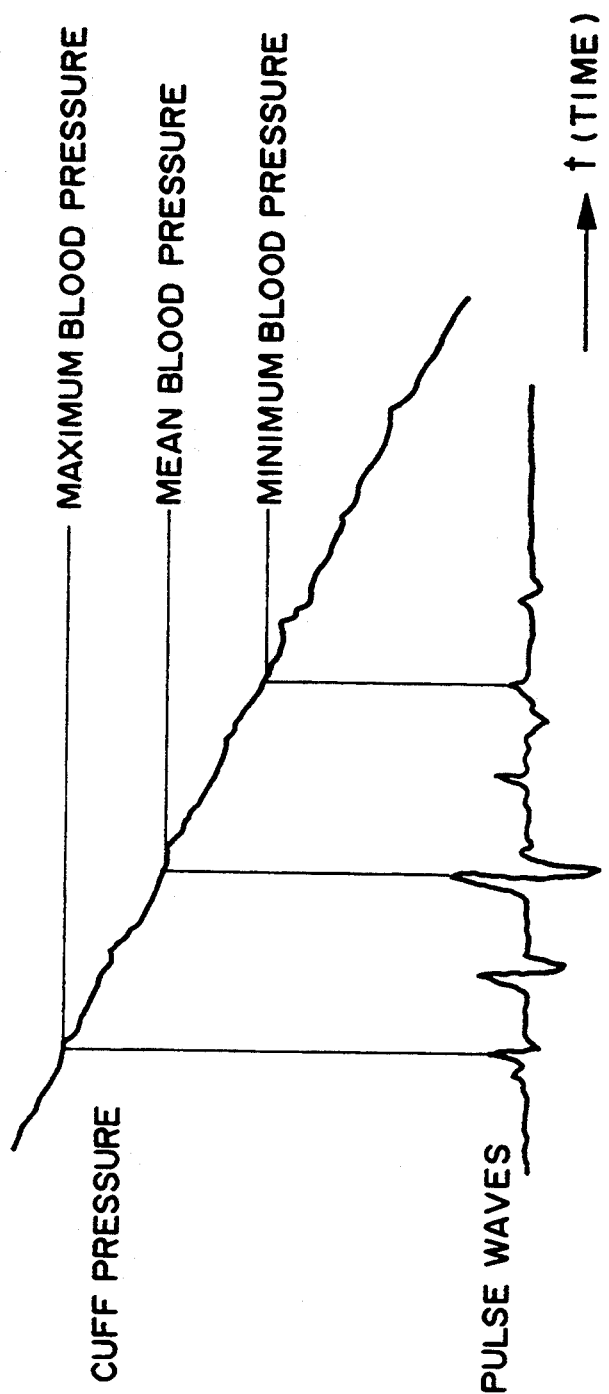
FIG. 7 is a diagram showing a change in the pulse waves during a decline in cuff pressure.

Processing for measuring blood pressure using the automatic sphygmomanometer and the method of detecting an appropriate value of pressurization set forth above will now be described with reference to the flowcharts of FIGS. 4 through 6. The processing described below is executed by the controller 51 of the automatic sphygmomanometer.

First, when power is applied to the automatic sphygmomanometer at step S100, processing for initially setting the sphygmomanometer is started at step S110. In the initial-setting processing, the LCD 8 is checked at step S111, the buzzer is checked at step S112, and the lamp 7 which indicates that blood-pressure measurement is in progress is turned on at step S113. Then, at step S114, a pressure zeroing adjustment is performed so as to make the internal pressure of the cuff zero.

The processing proceeds from step S110 to step S120, at which the exhaust valve 24 is closed and the pump 22 driven into operation to start inflation of the cuff. At this time, processing for checking the batteries is started along with the start of pump drive. The checking of the batteries is performed constantly during operation of the pump.

In the processing for checking the batteries, it is examined at step S300 whether the power-supply voltage (V) is less than $4X$, which is a first threshold value. If $V \geq 4X$ is found to hold, it is judged that the batteries are in a normal state and the checking of the batteries is terminated. On the other hand, if $V < 4X$ is found to hold, the batteries are regarded to be low in energy and the processing proceeds to step S310, at which an indicator mark calling for replacement of the batteries is made to flash on the LCD 8 to warn the user of the automatic sphygmomanometer. At step S320, it is examined whether the power-supply voltage (V) is less than $4Y$, which is a second threshold value. If $V \geq 4Y$ is found to hold, it is judged that the pump is capable of operating even though the power of the batteries is low, and the processing for checking the batteries terminates. The processing proceeds only to warn the user. If $V < 4Y$ is found to hold, on the other hand, it is judged that pump operation is no longer possible and the processing proceeds from step S320 to step S330, at which the pump 22 is shut down and the exhaust valve 24 is opened. Next, at step S340, the buzzer 9 is sounded for a predetermined period of time, after which the buzzer is deactivated at step S350. This is followed by step S360, at which the display of cuff pressure value is removed from the LCD 8. Finally, at step S370, the battery replacement mark being displayed on the LCD 8 is changed from the flashing state to a steady state. The battery checking processing is then terminated.

The processing of steps S130 to S150 is executed at a suitably short time interval ($\Delta t$). If the batteries are in a normal state, the internal pressure value of the cuff is displayed at step S130 during inflation. This is followed by verification of pulse-wave amplitude at step S140. It is then examined at step S150 whether the current internal pressure of the cuff has attained an appropriate value of inflation. The determination at step S150 is made based upon the above-described method of detecting the appropriate pressure value of the cuff 2. That is, the value $[A(n+1)/A(n)] \times 100$ is obtained at the short time intervals $\Delta t$, where $A(n)$ is the pulse-wave amplitude, and $A(n+1)$ is the pulse-wave amplitude of the successive pulse after the pulse of $A(n)$. If this value is less than about 50~ about 70%, it is judged that internal cuff pressure has exceeded the systolic blood pressure. If a judgment is rendered to the effect that internal cuff pressure has not attained the systolic blood pressure, the processing returns to step S130 and inflation of the cuff continues. On the other hand, if it is judged that internal cuff pressure has exceeded the systolic blood pressure, then the processing proceeds to step S160, where the pump 22 is halted to terminate the inflation of the cuff.

Thus, when the internal cuff pressure has been raised to an appropriate value, processing makes a transition from measurement of systolic blood pressure to measurement of diastotic blood pressure. In this embodiment, the measurement of systolic and diastolic blood pressure is in accordance with the conventional Korotkoff method, which is based upon detection of Korotkoff sounds by the microphone 4.

Systolic blood pressure is measured at steps S170 and S180, after which diastolic blood pressure is measured at steps S190 and S200. When measurement ends, the exhaust valve 24 is opened at step S210 to vent the air from within the cuff. The internal cuff pressure continues to be reduced, while being displayed on the LCD 8 at step S220, until the internal cuff pressure is identified to fall below a predetermined pressure (20 mmHg in this embodiment) at step S230.

Finally, at step S240, the measured systolic blood pressure, diastolic blood pressure value and pulse rate are displayed alternately on the LCD 8 and the processing for measuring blood pressure is terminated.

Thus, in accordance with this embodiment, control is performed in such a manner that the cuff is inflated at a fairly rapid rate (30~40 mmHg/sec), the pulse waves are detected during inflation of the cuff, and inflation is terminated upon detecting, from the variation in the pulse waveform, a sudden decline in the pulse-wave amplitude observed when the patient's systolic blood pressure is exceeded. As a result, the optimum inflation of the cuff dependent upon the patient's systolic blood pressure can be achieved, and blood pressure can be measured in a short period of time.

In this embodiment, a case is described in which a detected pulse wave is compared with the pulse wave of the immediately preceding beat and, when pulse-wave amplitude has diminished in excess of a predetermined level (found experimentally to be about 50~ about 70% of the pulse-wave amplitude which prevailed at the preceding beat), it is judged that the systolic blood pressure has been exceeded, whereuponinflation of the cuff is terminated. However, the present invention is not limited to such an arrangement. For example, it is known statistically that pulse-wave amplitude when systolic blood pressure is attained is about 50 to about 80% of the maximum pulse-wave amplitude. By utilizing this fact, it is also possible to perform control in such a manner that inflation of the cuff is terminated when pulse-wave amplitude falls below about 50% of the maximum pulse-wave amplitude. Furthermore, because the method of deciding the cuff inflation cut-off point by measurement of pulse-wave amplitude for only one beat is susceptible to the influence of disturbances in the pulse waves, as ascribable to the patient's body movement, and this can lead to an erroneous judgment, it is possible to adopt an arrangement in which control is performed in such a manner that cuff inflation is terminated only when the pulse-wave amplitude satisfies prescribed conditions for two consecutive beats.

As many apparently widely different embodiments of the present invention can be made without departing from the spirit and scope thereof, it is to be understood that the invention is not limited to the specific embodiments thereof except as defined in the appended claims.

What is claimed is:

1. An automatic sphygmomanometer having a cuff which is fixable to a living body for receiving pulse waves from the living body, pressurizing means for supplying an interior portion of the cuff with pressurized air, cuff-pressure detecting means for detecting a pressure of the pressurized air within the cuff, and venting means for venting the pressurized air from the interior of the cuff, said automatic sphygmomanometer further comprising:

pulse-wave detecting means for detecting pulse waves from a living body, based upon the cuff pressure detected by said cuff-pressure detecting means, during inflation of the cuff by said pressurizing means;

measurement means for measuring an amplitude of the detected pulse waves;

calculation means for calculating a rrate of change in the measured amplitude of the detected pulse waves;

comparing means for comparing the calculated rate of change with a predetermined threshold value, and for outputting a comparison output;

discrimination means for discriminating whether or not an interior pressure of the cuff is beyond a systolic blood pressure of the living body, based on the comparison output, and for outputting a discrimination output; and control means for controlling said pressurizing means, in accordance with the discrimination output, in such a manner that inflation of the cuff by said pressurizing means is halted;

wherein said calculation means includes means for calculating the rate of change from a change in the measured amplitude of the detected pulse waves from one pulse of said detected pulse waves to a successive pulse of said detected pulse waves, and said predetermined threshold value is set to be 0.5 to 0.7, based on a ratio of the amplitude of said one pulse to the amplitude of said successive pulse.

2. The automastic sphygmomanometer according to claim 1, wherein said pressurizing means includes means for inflating the interior portion of the cuff at a speed of approximately 30~40 mmHg/sec.

3. The automatic sphygmomanometer according to claim 1, further comprising:

measuring means for measuring at least one of a systolic blood pressure and a diastolic blood pressure after inflation of the cuff by said pressurizing means is halted; and display means for displaying the at least one of the systolic blood pressure and diastolic blood pressure measured by said measuring means.

4. The automatic sphygmomanometer according to claim 3, wherein said display means comprises an LCD.

5. The automatic sphygmomanometer according to claim 1, wherein said discrimination means comprises means for discrminating that the interior pressure of the cuff is beyond the systolic blood pressure of the living body when the comparison output indicates that the calculated rate of change exceeds the predet4rmined threshold value, and means for outputting a discrimination output responsive thereto that indicates to the control means that inflation of the cuff by said pressuring means is to be halted.

6. A method of measuring blood pressure comprising:

a pressurizing step of supplying an interior portion of a cuff, which is affixed to a living body, with pressurized air to inflate the cuff;

a detecting step of detecting pulse waves from the living body during inflation of the cuff;

a calculating step of calculating a rate of change in an amplitude of the detected pulse waves;

a comparing step of comparing the calculated rate of change with a predetermined threshold value, and outputting a comparison output;

a discrimination step of discriminating whether or not an interior pressure of the cuff is beyond a systolic blood pressure of the living body, based on the comparison output, and outputting a discrimination output;

a stopping step of stopping inflation of the cuff based on the discrimination output; and a measuring step of measuring at least one of a systolic blood pressure and diastolic blood pressure after inflation of the cuff is stopped, wherein said calculating step comprises calculating the rate of change from a change in the amplitude of the detected pulse waves from one pulse of said detected pulse waves to a successive pulse of said detected pulse waves, and said predetermined threshold value is set to be 0.5 to 0.7, based on a rateio of the amplitude of said one pulse to the amplitude of said successive pulse.

7. The method according to claim 6, wherein when the comparison output indicates that the calculated rate of change exceeds the predetermined value, the discrimination step comprises discriminating that the interior pressure of the cuff is beyond the systolic blood pressure of the living body, and outputting a discrimination output that indicates that inflation of the cuff is to be stopped.

* * * * *

UNITED STATES PATENT AND TRADEMARK OFFICE
CERTIFICATE OF CORRECTION

PATENT NO. : 5,335,665
DATED : August 9, 1994
INVENTOR(S) : SUZUKI, Seigo

It is certified that error appears in the above-indentified patent and that said Letters Patent is hereby corrected as shown below:

On the Title page, Item [56], References Cited,

Under "U.S. PATENT DOCUMENTS" insert:
    --4,461,266  7/1984  Hood Jr. et al--

Under "FOREIGN PATENT DOCUMENTS", insert:
    --332,701  9/1989    EPA--

Column 4, line 1, "20" should be --2.--

Column 6, line 67,
    "whereuponinflation" should be --whereupon inflation--

Column 8, line 21 (claim 5), "predet4rmined" should be --predetermined--

Signed and Sealed this

Second Day of January, 1996

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,335,665
DATED : 9 AUG 1994
INVENTOR(S) : SUZUKI

It is certified that error appears in the above-indentified patent and that said Letters Patent is hereby corrected as shown below:

In the title page, under Section [56]

References Cited FOREIGN PATENT DOCUMENTS,

Change "59-19692" to --59-19691--; and

Change "61-4-416" to --61-40416--

Signed and Sealed this

Twenty-third Day of January, 1996

*Attest:*

BRUCE LEHMAN

*Attesting Officer*     *Commissioner of Patents and Trademarks*